United States Patent [19]

Schankereli

[11] Patent Number: 5,782,914
[45] Date of Patent: Jul. 21, 1998

[54] METHOD FOR PREPARING HETEROGENEOUS TISSUE GRAFTS

[75] Inventor: Kemal Schankereli, Stillwater, Minn.

[73] Assignee: Bio-Vascular, Inc., St. Paul, Minn.

[21] Appl. No.: 764,686

[22] Filed: Nov. 29, 1996

[51] Int. Cl.$^6$ ........................................ A61F 2/02
[52] U.S. Cl. ............................ 623/11; 623/1; 623/2; 623/13; 623/66; 623/901; 435/1
[58] Field of Search ........................ 623/2, 4, 66, 1, 623/11–15, 901; 435/1

[56] References Cited

U.S. PATENT DOCUMENTS

| | | |
|---|---|---|
| 3,318,774 | 5/1967 | Dingwall et al. . |
| 3,491,760 | 1/1970 | Braun et al. . |
| 3,842,831 | 10/1974 | Beisang et al. . |
| 4,300,243 | 11/1981 | Baumgartner . |
| 4,399,123 | 8/1983 | Oliver et al. . |
| 4,442,655 | 4/1984 | Stroetmann . |
| 4,448,718 | 5/1984 | Yannas et al. . |
| 4,553,974 | 11/1985 | Dewanjee . |
| 4,597,762 | 7/1986 | Walter et al. . |
| 4,681,588 | 7/1987 | Ketharanathan . |
| 4,969,912 | 11/1990 | Kelman et al. ............... 623/66 |
| 4,994,084 | 2/1991 | Brennan . |
| 5,031,762 | 7/1991 | Heacox ........................ 623/15 |
| 5,066,578 | 11/1991 | Wikman-Coffelt ............ 435/1 |
| 5,108,424 | 4/1992 | Hoffman, Jr. et al. . |
| 5,139,527 | 8/1992 | Redl et al. . |
| 5,326,350 | 7/1994 | Li .................................. 623/11 |
| 5,330,974 | 7/1994 | Pines et al. . |
| 5,336,616 | 8/1994 | Livesey et al. . |
| 5,350,583 | 9/1994 | Yoshizato et al. . |
| 5,507,810 | 4/1996 | Prewett et al. ................ 623/11 |
| 5,513,662 | 5/1996 | Morse et al. .................. 623/16 |
| 5,554,185 | 9/1996 | Block et al. ................... 623/2 |
| 5,585,116 | 12/1996 | Boniface et al. .............. 623/16 |

*Primary Examiner*—Michael J. Milano
*Assistant Examiner*—Tram Anh T. Nguyen
*Attorney, Agent, or Firm*—Fredrikson & Byron, P.A.

[57] ABSTRACT

A method for preparing heterogeneous graft material from animal tissue in which the harvested tissue is cleaned, chemically cross-linked and then vacuum-dried to remove substantially all moisture therefrom. The vacuum-dried animal tissue is then double-wrapped and subjected to radiation sterilization while in its packaged dry state. Electron beam sterilization is a preferred method. At the time of use, the outer wrap is opened and the inner sterile package is placed in the sterile field in the operating room. When the tissue specimen is removed from its inner wrap, it may be rehydrated in sterile saline to restore its soft, supple hand, or it may be implanted in its dry state at the implanting surgeon's discretion, in which case, the tissue would undergo rehydration with the patient's own body fluids.

12 Claims, 2 Drawing Sheets

METHOD FOR PREPARING HETEROGENEOUS TISSUE GRAFTS

BACKGROUND OF THE INVENTION

I. Field of the Invention

This invention relates generally to a method for preparing animal tissue for use as a graft material, and more particularly to a method for preparing a heterogeneous graft material that can be packaged in a sterile container in a dry state for shipping and storage and subsequently rehydrated at the time of surgical implantation.

II. Discussion of the Prior Art

In a copending application of Joel Cooper, et al., Ser. No. 08/194,382, filed Feb. 10, 1994, now U.S. Pat. No. 5,503,638, and assigned to applicants' assignee, there is described a tissue specimen especially intended for use in buttressing a staple line used to close a surgically created wound in an organ. For example, during lung surgery, where a portion of diseased lung tissue is excised, a tissue specimen formed by processing pericardial or dura mater tissue of a slaughtered animal may be placed about the jaws of a conventional surgical staple gun and the staples fired through the specimen material along the border of the lung tissue to be closed. As is explained in the aforereferenced application, the use of the reinforcing tissue specimen is found to create a stronger, more fluid-impervious closure than when staples alone are used.

Prior to the present invention, the tissue specimens were prepared by first harvesting the selected tissue from beef cattle or other meat supplying animals at the slaughter house. The harvested tissues were then transported to a laboratory where the material was cleaned by mechanically stripping away fat tissue and other undesired components from the harvested specimen material. Next, the cleaned tissue specimen was subjected to a cross-linking operation in which it is soaked for a predetermined time in a glutaraldehyde solution and finally was dehydrated in an alcohol solution. Subsequently, the sample was thoroughly rinsed to remove traces of the ethyl alcohol and glutaraldehyde and then was packaged in a vial containing a one percent propylene oxide solution as a sterilant. At the time of use, operating room personnel would have to open the vial and remove the tissue specimen without having it contact the non-sterile exterior of the vial. It would also be necessary to dispose of the liquid sterilant. The tissue specimen would then have to be rinsed in sterile saline to remove all traces of the propylene oxide and other processing reagents from the specimen before it was ready to be used in carrying out the surgical procedure.

Another drawback of wet packaging of products centers on shipping and handling concerns. In shipping into or from colder climates, freezing and breakage of the glass vials can be a problem. Furthermore, the packaging tends to be bulky, heavy and hard to store. When the method described in the Cooper et al. application for mounting a wet tissue specimen to the jaws of a surgical stapler is followed, it is necessary to form a sleeve using a suitable backing material stitched to the tissue specimen. With a dry specimen, an adhesive layer can be applied to the specimen, either at the time of manufacture or at the time of implant, allowing the specimen to be affixed to the stapler and obviating the need for a backing material and simplifying the surgery. Thus, at the time the present invention was made, a need existed for a method of producing a tissue specimen material that could be packaged in a dry state in a double-wrapped container and subsequently sterilized so that both the tissue specimen and the inner container remained sterilized when subsequently opened in an operating room and placed in sterile saline and rehydrated to exhibit the same physical properties as the prior art product packaged in a wet state.

SUMMARY OF THE INVENTION

The present invention comprises a method of preparing animal tissue for use in surgical procedures on humans so that it can be shipped and stored in a dry state prior to use and comprises the steps of first harvesting a predetermined segment of animal tissue (hereinafter referred to as a tissue specimen) from a domesticated animal at the time of slaughter of that animal and subsequently cleaning the tissue specimen to remove unwanted tissue components such as fatty deposits and the like therefrom. Following the cleaning operation, the tissue specimen is first subjected to a chemical cross-linking step, preferably by soaking the tissue specimen for a predetermined length of time in a glutaraldehyde solution of a predetermined concentration. Once the cross-linking has taken place and the tissue specimen rinsed to remove traces of the tanning solution, it is then soaked in a 70% $E_tOH$ solution for a predetermined time period in a range of from ten hours to several days, which serves to remove bioburden and to kill any microbes theretofore present in the tissue material. Next, the specimen is mounted in a frame and placed in a vacuum drying chamber which is then evacuated to a predetermined vacuum level sufficient to dry the cross-linked tissue specimen. The vacuum-dried tissue specimen is subsequently removed from the vacuum chamber and trimmed to the appropriate dimensions. At this point, a suitable adhesive may be applied to one surface of the specimen, if desired. It is then placed in a package in its dried state. Both the package and the tissue specimen contents may then be subjected to radiation or ethylene trioxide sterilization.

Tissue specimens formed in accordance with the above process have the feel and appearance of leather, but when placed in a hydrating fluid, such as sterile saline, for a period of time measured in minutes, the tissue specimen exhibits substantially the same hand, i.e., texture and feel that the prior art product had when processed and stored in a wet condition as earlier described in the "Discussion of the Prior Art".

DESCRIPTION OF THE DRAWING

The foregoing features and advantages of the invention will become apparent to those skilled in the art from the following detailed description of a preferred method of manufacture, especially when considered in conjunction with the accompanying drawing in which FIGS. 1(A) and 1(B) when arranged as shown in FIG. 1 illustrates by means of a process flow chart, the steps employed in producing heterogeneous graft material for use in surgical procedures.

DESCRIPTION OF THE PREFERRED EMBODIMENT

Figure 1A:
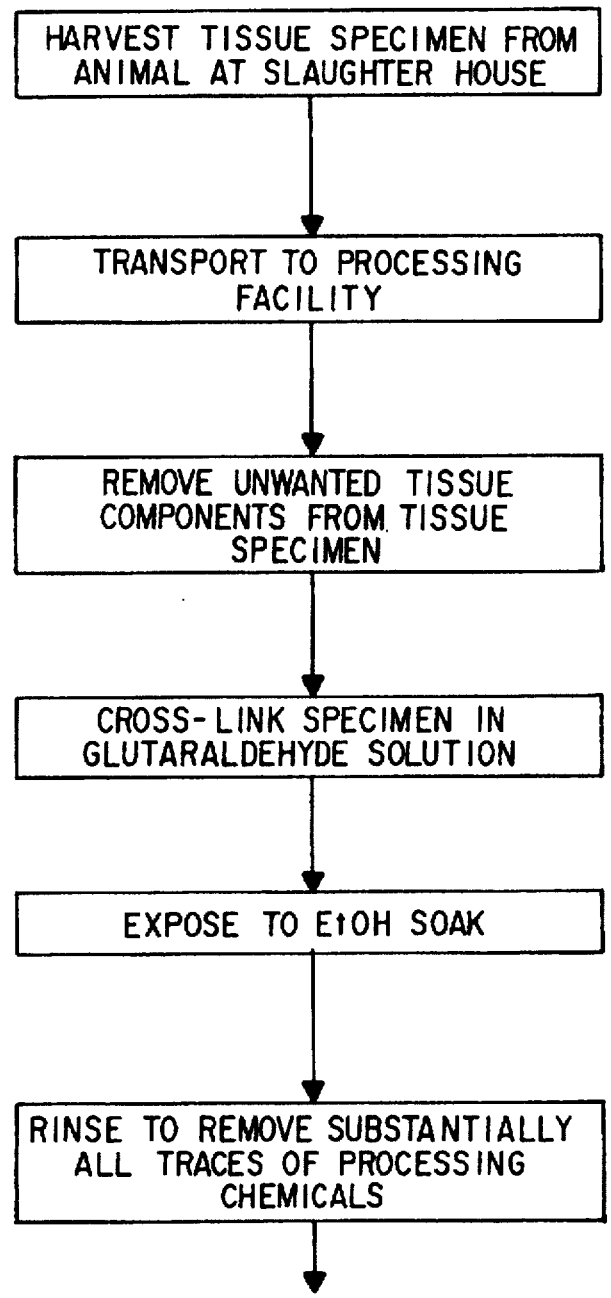
Figure 1B:
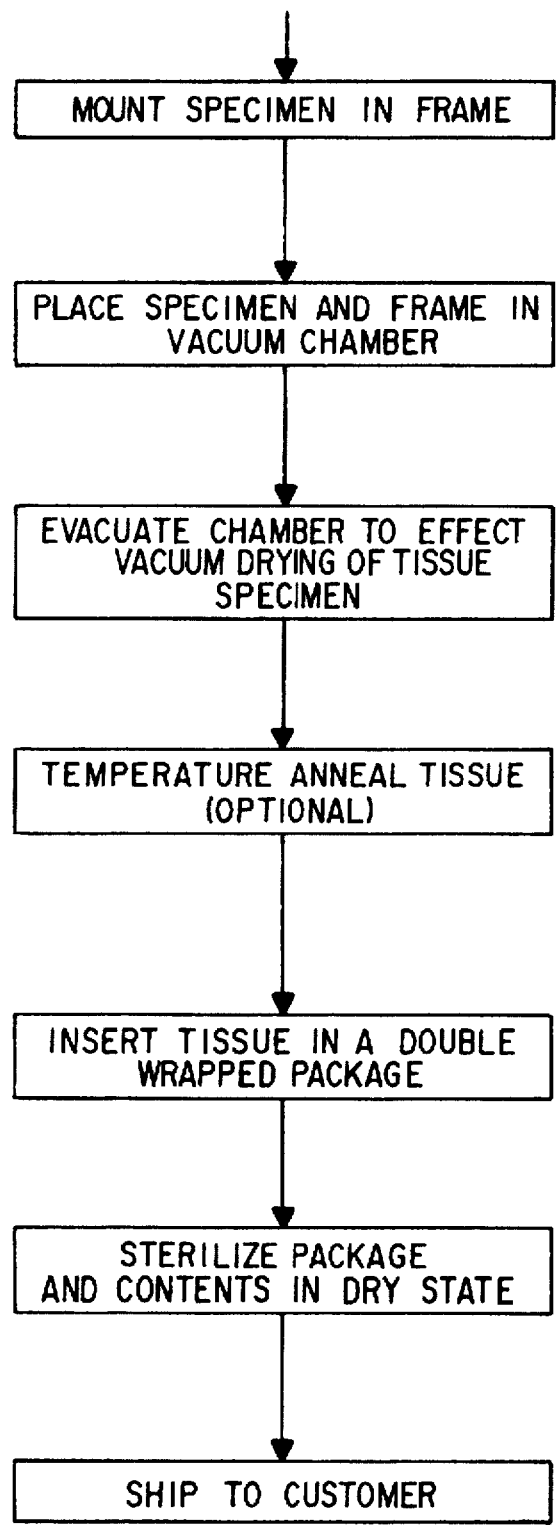

With reference to the flow diagram shown in the accompanying drawing, the method for preparing animal tissue for later use as a heterogeneous graft in human subjects in accordance with the present invention is illustrated. In carrying out the method, arrangements are made with a slaughter house company to harvest desired tissue materials from domesticated animals, such as beef cattle, pigs and sheep. For example, pericardial tissue dura mater fascia may be harvested and frozen or cooled on ice for transport to a processing facility where the tissue is further processed in creating a sheet-type heterogeneous graft. Those skilled in the art can appreciate that the method of this invention can be applied to other animal tissues, including arteries, veins, tendons, ligaments, heart valves, etc.

Upon arrival at the processing facility, the harvested tissue material is thawed, if necessary, and cleaned by removing unwanted tissue components, such as fat, blood, and other unwanted contaminants. The removal may be mechanical as by cutting and trimming away the unwanted tissue and washing the tissue specimen.

As an optional step, the thus-cleaned tissue material may be dehydrated in an ethanol solution wherein fluids on and in the tissue specimen may be replaced by ethanol. This inhibits microbial contamination in the event of in-process storage.

Irrespective of whether the dehydration step is utilized, the specimen is next subjected to a cross-linking operation by soaking it in a aqueous solution of glutaraldehyde. Typically, the solution may comprise 0.25% buffered glutaraldehyde and the balance water. The specimen is left to soak for a period in the range of from 1 to 120 hours, a time sufficient to effect cross-linking.

Upon completion of the cross-linking step, the specimen may again be immersed in a 70% ethanol 1% propylene oxide solution for up to two weeks to resist any chance for microbial contamination. It is later rinsed in sterile water for about two hours to reduce any traces of the processing chemicals and then is mounted in a frame between perforated stainless steel sheets or fine mesh stainless steel screens to stabilize the shape and thickness of the specimen. The frame containing the tissue specimen is then placed in a vacuum chamber and the interior thereof is evacuated to a predetermined negative pressure in the range of from 0 to 700 mTorr over a predetermined time period in a range of from 0.5 to 5.0 hours, whereby substantially all solvent is volatilized and removed from the specimen. Good results have been achieved by drawing a vacuum in the range of from 100 to 200 mTorr for a period of from 1.5 to 2 hours with a drying temperature target in a range of from +22° C. to 27° C. Those skilled in the art will appreciate that the times involved depend on the size and number of specimens being treated in the vacuum chamber in that the quantity of water to be removed is dependent on the size and number.

Once vacuum drying of the tissue is complete, the interior of the chamber is returned to ambient pressure and the tissue specimens are removed from the chamber. This process decreases the moisture content of the specimen from about 70% to about 10% by weight.

If the tissue sample is unacceptable for an intended application because the specimen is unduly wrinkled, an optional temperature annealing step may be used to improve the flatness characteristic of the tissue specimen. Specifically, the tissue sample is placed in a holder and then heated to a temperature of approximately 50° C. with that temperature being maintained for about one hour.

The product is then inserted in a first, moisture-proof sterilizing pouch which may be evacuated. This pouch is then placed within a second, outer moisture-proof sterilizing pouch, and similar packages containing vacuum-dried tissue specimens are packed in shipping cartons and sent out for dry sterilization. In this regard, a form of radiation sterilization is preferred with electron beam sterilization being the most favored approach. In particular, by subjecting the carton and its contents to an exposure in the range of from 10 to 35 kiloGray (1 to 3 megarads) for a period in the range of from 0.5 to 20 minutes (depending upon package dimensions), the packaged tissue specimens, as well as the double layer package itself, is effectively rendered sterile. Because the dose rate for a typical e-beam is about 75 times greater than that from a gamma radiation source, the sterilization time using e-beam radiation is dramatically lower than what is required for gamma radiation. Evacuation and/or replacement of the atmosphere within the tissue package (the package containing the dried tissue) using a media such as argon or nitrogen limits free radical formation (oxidation) of the tissue during the sterilization process thus inhibiting chemical and physical changes to the tissue. Free radical formation reactions are common with low dose rate/long exposure time gamma radiation sterilization. E-beam radiation as a dry sterilization process affords the further advantage in terms of ease and safety of operation. The energy used in typical e-beam processing (usually 10 MeV or less) is insufficient to cause activation (induced radioactivity) of irradiated materials. Since there is no radioactive source, no specific handling, monitoring or disposing requirements are necessary. When the power to the electron beam accelerator is turned off, no radiation hazard is present.

Another important consideration in the choice of radiation sterilization is the expected temperature rise resulting from the radiation. This is especially true where the material to be sterilized is a collagen-based material. An excessive temperature rise may result in denaturation of the protein. Because the time required to sterilize is substantially shorter with e-beam radiation (minutes compared to hours), the time that the material would be required to remain at a somewhat elevated temperature is considerably longer in the case of gamma radiation when compared to e-beam radiation.

At the time of use, the outer package may be opened with the inner package being placed into the sterile field in the operating room. The inner sterile package is then opened and the contents removed and placed in a sterile saline solution whereupon the tissue specimen is again hydrated and ready for use in the surgical procedure as a heterogenous graft. The vacuum-dried tissue may also be placed on a dry sterile field if the attending surgeon prefers to implant the product dry, as the procedure may require. Where it is possible that some surgical procedures will not require the use of adhesives in conjunction with the dry tissue, it will be advantageous to use an adhesive in some applications. For instance, preparation of the dry tissue for lung volume reduction may necessitate adhering the tissue onto the jaws of a stapler using an adhesive. In this case, it is envisioned that the dry product will be removed from its packages, and an adhesive such as hydrogel be applied directly onto the dry material. The dried tissue/adhesive composite will be placed directly onto the faces of the stapler. Clamping the composite tissue/adhesive using the normal closing force of the stapler will serve to affix the tissue onto the stapler faces. The tissue may become partially hydrated from transfer of water out of the adhesive into the tissue. The tissue is positioned and firing of the stapler is accomplished as usual. Once positioned in situ the tissue becomes fully hydrated. One favorable composition of adhesive can be constructed from hydroxypropylmethycellulose in conjunction with propylene glycol and water. Depending upon the concentrations of chemicals used, the hydration capabilities and tack of the adhesive can to an extent be modified in accordance to the needs of the application. Of course, a suitable adhesive material, e.g., a natural rubber, a synthetic adhesive or a hydrogel, may be applied to a surface of the tissue specimen prior to its being placed in its package and sterilized rather than at its time of use.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

For example, the order in which certain steps are carried out can be changed. Specifically, following completion of the glutaraldehyde cross-linking step, the rinsing step and the ethanol soak, the specimen may be mounted in a drying cassette (frame). As such, the freeze drying can take place with the specimen already in an envelope or pouch.

What is claimed is:

1. A method of preparing animal tissue for use in surgical procedures on humans comprising the steps of:
   (a) harvesting a predetermined tissue specimen from a domesticated animal at the time of slaughter of such animal;
   (b) cleaning the tissue specimen to remove unwanted components;
   (c) chemically cross-linking the cleaned tissue specimen;
   (d) extracting bioburden from the tissue specimen by exposing the tissue to an ethanol soak for a predetermined time,
   (e) rinsing away processing chemicals used in steps (c) and (d);
   (f) placing the tissue specimen from step (e) in a vacuum chamber;
   (g) evacuating the vacuum chamber to a predetermined vacuum level for a predetermined time sufficient to vacuum-dry the cross-linked tissue specimen;
   (h) bringing the vacuum chamber back to ambient pressure and removing the vacuum-dried tissue specimen from the chamber;
   (i) placing the vacuum-dried tissue specimen in a package; and
   (j) radiation sterilizing the packaged tissue specimen.

2. The method as in claim 1 wherein the domesticated animal is a member of the group consisting of bovine, porcine and ovine animals.

3. The method as in claim 2 wherein the harvested tissue specimen comprises a collagen-based tissue selected from the group consisting of pericardium, dura mater, heart valves, blood vessels, fascia, ligaments, tendons, and pleura tissue.

4. The method as in any one of claims 1 through 3 wherein chemically cross-linking the cleaned tissue specimen includes soaking the cleaned tissue specimen in an aqueous solution of glutaraldehyde for a predetermined time.

5. The method as in claim 4 wherein the aqueous solution includes 0.001–2% glutaraldehyde and the predetermined time is in the range of from 24–120 hours.

6. The method as in claim 5 and further including the step of rinsing the cross-linked tissue specimen to substantially remove all traces of the glutaraldehyde solution.

7. The method as in claim 6 and further including the step of mounting the rinsed tissue specimen in a frame prior to placement of the tissue rinsed specimen in the vacuum chamber to prevent wrinkling and shrinkage thereof.

8. The method as in claim 4 wherein the aqueous solution includes 0.25% glutaraldehyde and the predetermined time is in the range of from 1 to 120 hours.

9. The method as in claim 1 wherein the predetermined vacuum level is in the range of from 0 to 700 mTorr and the predetermined time is in the range of from 0.5 to 5 hours.

10. The method as in any one of claims 1–3 and further including the step of dehydrating the cleaned tissue specimen subsequent to the chemical cross-linking thereof.

11. The method as in any one of claims 1–3 wherein the step of radiation sterilizing the packaged tissue specimen comprises exposing the package and its contents to an electron beam for a time sufficient to sterilize the package and its contents.

12. The method as in claim 11 wherein the exposure is in the range of from 10 to 35 kiloGray over a period of time necessary to achieve a required dose.

* * * * *